United States Patent
McErlean et al.

(10) Patent No.: US 9,498,284 B2
(45) Date of Patent: Nov. 22, 2016

(54) TREATING AND PREVENTING NAIL DISORDERS

(75) Inventors: Eamon McErlean, Alloa (GB); Gary Beale, Stirling (GB)

(73) Assignee: EMBLATION LIMITED (GB)

(*) Notice: Subject to any disclaimer, the term of this patent is extended or adjusted under 35 U.S.C. 154(b) by 1179 days.

(21) Appl. No.: 13/483,266

(22) Filed: May 30, 2012

(65) Prior Publication Data

US 2012/0310231 A1 Dec. 6, 2012

Related U.S. Application Data

(60) Provisional application No. 61/491,496, filed on May 31, 2011.

(51) Int. Cl.
*A61B 18/18* (2006.01)
*A61B 18/00* (2006.01)

(52) U.S. Cl.
CPC .. *A61B 18/1815* (2013.01); *A61B 2018/00452* (2013.01)

(58) Field of Classification Search
CPC .............. A61B 18/1815; A61B 2018/00452
See application file for complete search history.

(56) References Cited

U.S. PATENT DOCUMENTS

| | | | | |
|---|---|---|---|---|
| 4,517,975 A | * | 5/1985 | Garito | A61B 17/54 219/234 |
| 5,683,386 A | * | 11/1997 | Ellman | A61B 18/1402 606/41 |
| 6,104,959 A | | 8/2000 | Spertell | |
| 7,292,893 B2 | * | 11/2007 | Hoenig et al. | 607/101 |
| 2008/0319517 A1 | * | 12/2008 | Cumbie | 607/88 |

OTHER PUBLICATIONS

"Phenol," HPA Compendium of Chemical Hazards, 2011, Version 4, 32 pages.
Chapeskie, "Ingrown Toenail or overgrown toe skin?," Canadian Family Physician, 2008, vol. 54, No. 11, pp. 1561-1562.
Clayton et al., *Patty's Industrial Hygiene and Toxicology*, 3rd Edition, J Wiley and Sons, New York, 1982, p. 2583.

* cited by examiner

*Primary Examiner* — Amanda Patton
(74) *Attorney, Agent, or Firm* — Sheridan Ross P.C.

(57) ABSTRACT

A method of treating or preventing a nail disorder comprises administering to a subject having/suffering from or susceptible/predisposed to, said nail disorder, a therapeutically effective amount or dose of microwave energy.

7 Claims, 6 Drawing Sheets

TREATING AND PREVENTING NAIL DISORDERS

CROSS REFERENCE TO RELATED APPLICATIONS

This application claims the benefit of priority to U.S. Provisional Patent Application No. 61/491,496, filed on May 31, 2011, the entire disclosure of which is incorporated herein by reference.

FIELD OF THE INVENTION

The present invention provides compositions, medicaments and methods for the treatment of disorders, conditions and/or diseases affecting keratinized structures or tissues such as nails. The invention further relates to apparatus for use in treating the same.

BACKGROUND TO THE INVENTION

Keratinised tissues and/or structures, in particular the nail, are prone to a range of diseases, conditions and/or disorders.

Ingrown nails (onychocryptosis) are a common problem that occurs when the nail embeds into the lateral nail groove and resulting in inflammation causing pain and discomfort along the margins of the nail. The main cause of onychocryptosis in toe nails is the wearing of unsuitable footwear that applies excessive side and or top pressures to the nail. Other causes include high levels of foot moisture softening the nail and extending the epidermis keratin which can change the convex arch permanently. Other causes include genetics, accidental trauma, incorrect nail trimming or disease. An alternative school of thought promoted by Vandenbos and Bowers (Can. Fam. Phys. 54 (11): 1561-1562) is that the "Ingrown Toenail" can result from excess skin forming around the nail and that the nail may not be the causative factor, they hypothesize that the soft tissue should be excised rather than the ingrown segment of the nail.

The most common therapy for onychocryptosis is phenolization which uses phenol (known as carbolic acid, hydroxybenzene, monohydroxybenzene, benezenol, $C_6H_5OH$) to permanently ablate the part of the nail matrix that makes the section of the ingrown nail. This technique is referred to as partial matrixectomy or phenol avulsion. The treatment using phenol can occasionally result in infection as it is invasive and damages the skin barrier and requires aftercare treatment. In some cases incorrect or inadequate treatment can result in partial regrowth of the nail which leads to recurrence of the condition as the re-growing nail fragment embeds into the nailfold. This requires repeat treatment to ensure that the treatment is effective. Caution must be taken with phenol as excess application has the potential to cause burns to surrounding tissues.

In chronic onychocryptosis cases a full nail removal (avulsion) is sometimes used to treat the problem. In this treatment the nail is removed and the full nail matrix is cauterised using a caustic agent (such as phenol or sodium hydroxide) to prevent the nail regrowing. Again in some instances incorrect or inadequate treatment can result in partial regrowth of the nail requiring repeat treatments to prevent recurrence.

There are a number of other treatments including the Vandenbos procedure where excess tissue around the nail is surgically excised and mechanical intervention treatments that involve correcting the shape of the nail or removing pressure caused by the nail against the nail fold. However these techniques are not widely employed and phenolization remains the treatment of choice.

Phenol is a highly caustic chemical and is also a VOC (Volatile Organic Compound), and phenol vapour is known to be harmful to the eyes, skin, respiratory system digestive system, heart, kidney, liver, lung, peripheral nerves, and the unborn child. Phenol is readily absorbed through the skin or through inhalation and prolonged inhalation of phenol vapour may cause digestive, nervous, skin, liver and kidney problems.

Whilst not classified as a human carcinogen, phenol has also been shown to cause cancer in laboratory animals, and may cause mutagenic effects, as reported by British Data Hazard database (EM Science database) and by Clayton & Clayton L V. *Patty's Industrial Hygiene and Toxicology*, $3^{rd}$ *Edition*, J. Wiley and Sons, New York, 1982. The Health and Safety Executive in the UK reviewed occupational exposure limits for phenol and could no longer identify a safe level, as a result they issued a chemical hazard alert notice for phenol in 2000. As of 2007 a long term work place exposure limit (LTEL, 8 hour reference period) for phenol was established of 2 ppm (8 mg m$^{-3}$). No short term exposure limit (STEL, 15 min reference period) guideline value has been specified. COSHH regulations state that Phenol must not be used if a safer, alternative substance is available, and minimal quantities must be used and stored in the workplace. In many workplaces user exposure is controlled through the frequent rotation of staff that use phenol.

Although this hazardous chemical is an effective and consistent treatment for onychocryptosis, it requires significant controls for use, storage and disposal.

Alternative treatments employ chemical or caustic agents including, sodium hydroxide, liquid nitrogen, urea and other highly acidic or alkaline compounds. Again these treatments require accurate control of the dosage to prevent excess damage and also require specialised storage and handling procedures for caustic chemicals and hazardous gases.

Other treatments include using energy to ablate the tissue and include using laser and radiofrequency (RF) electrosurgery. These treatments do have limitations. Laser treatment is often reported as having good efficacy however the results are often inconsistent based upon user feedback; additionally the systems are prohibitively expensive for most users. With RF ablation users have reported experiencing some problems including nail regrowth and pain. Overaggressive RF electrocautery to the nail matrix can damage the fascia or periosteum underlying the nail matrix.

One of the limitations of RF ablation is that it requires a current path to be established using a grounding pad (Neutral Plate) to conduct the energy from the tissue. This can often cause problems as poor contact with the grounding pad can limit the energy delivered leading to inconsistent treatments and unreliability and in some cases a poorly contacting grounding pad can cause secondary burns from the exit current.

A more suitable treatment would be one where energy can be deposited in a repeatable and controlled manner to a predetermined depth or having a consistent dosage.

SUMMARY OF THE INVENTION

The present invention is based on the finding that microwave energy may be used to treat or prevent diseases, conditions and/or disorders affecting keratinized tissues and/or structures, in particular, diseases, conditions and/or disorders of the unguis (or nail or nails).

As such, a first aspect of the invention provides a method of treating or preventing a disease, disorder and/or condition of the nail, said method comprising administering to a subject having or suffering from said disease, condition and/or disorder of the nail or a subject susceptible/predisposed thereto, a therapeutically effective amount or dose of microwave energy.

In a second aspect, the invention provides microwave energy for use in treating or preventing a disease, disorder and/or condition of the nail.

For convenience, a "disorder, disease and/or condition of the nail" will hereinafter be more generally referred to as a "nail disorder".

A nail disorder may include any disorder affecting the structure of the unguis or nail and/or tissues associated therewith. As such nail disorders according to this invention may comprise disorders affecting one or more of the structures and/or tissues selected from the group consisting of: the matrix (matrix unguis); the nail bed; the nail plate (corpus unguis); the lunula, the nail sinus (sinus unguis); the nail root (radix unguis); and the paronychium. It should be noted that the above detailed list is not exhaustive and the invention extends to the treatment and/or prevention of any disorders affecting structures and/or tissues associated with the nails. Accordingly, the invention encompasses disorders of the finger and/or toe nails.

While the invention relates to the treatment of human nail disorders, one of skill will appreciate that the invention may extend to the treatment and/or prevention of disorders affecting analogous structures and/or tissues present in animals—particularly mammals and those collectively known as ungulates. For example, the invention may extend to the treatment of disorders affecting talon, claw and/or hoof structures and/or associated tissues.

In one embodiment, the invention described herein may find particular application in the treatment or prevention of onychocryptosis, characterised by ingrown nails.

In view of the above, the invention relates to microwave energy for use in treating or preventing onychocryptosis.

Moreover, the invention provides a method of treating or preventing onychocryptosis, said method comprising administering to a subject having or suffering from or susceptible/predisposed to onychocryptosis, a therapeutically effective amount or dose of microwave energy.

In a further embodiment, the nail disorders described herein and in particular, onychocryptosis, may occur as a complication following a cell/tissue proliferation and/or differentiation disorder such as, for example, cancer and/or a microbial (viral, bacterial and/or fungal) infection. Cancers which might lead to a nail disorder such as onychocryptosis may include, for example, squamous cell carcinoma of the nail bed or subungal melanoma. In some cases, the nail disorder may occur following the appearance of benign or malignant lesions.

Microbial infections which might lead to the development of a nail disorder such as onychocryptosis, may include fungal (such as fungal nail (dermatophyte) infections including onychomycosis), bacterial and/or viral infections.

It should be noted that where the nail disorder occurs as a consequence of some underlying condition such as, for example, the occurrence of a cell proliferation disorder or a microbial infection, the invention described herein (namely the application of microwave energy) is used to treat or prevent the nail disorder and not an underlying condition. As such, in certain embodiments, the invention may not extend to the treatment of nail fungal infections.

In addition to the various uses described herein, it should be understood that the invention also relates to methods of treating or preventing any of the diseases and/or conditions described herein, wherein the methods comprise administering to a subject in need thereof (i.e. a subject who is suffering from or susceptible/predisposed to any of the diseases/conditions described herein) a therapeutically effective amount or dose of microwave energy. As such, the invention provides methods of treating or preventing, for example, onychocryptosis.

One of skill will appreciate that in order to treat and/or alleviate the symptoms any of the diseases and/or conditions described herein (including, for example, onychocryptosis) one or more treatments with microwave energy may be required.

With regard to the treatment of onychocryptosis and without wishing to be bound by theory, the inventors hypothesise that the induction of hyperthermia by targeted application of microwave energy, irreparably damages the radix unguis preventing division of the germinative layer of the underlying epidermis which in turn prevents formation of the corpus unguis.

Localized thermal increase can be achieved using a precise deposition of energy to the sinus unguis targeting the radix unguis, readily achievable using microwave energy.

As stated, the invention relates to the treatment and/or prevention of nail disorders including, for example, onychocryptosis by exploiting the ability of microwave energy to prevent the growth of all or a portion/segment of the radix unguis. However, the present invention may additionally give rise to a therapeutic effect (particularly in the treatment of conditions such as onychocryptosis) via the targeted application of microwave energy to induce hyperthermia destroying excess paronychium tissue. In this way, it may be possible to use microwave energy to relieve pressure on the nail as might occur in onychocryptosis.

In a further aspect, the invention provides a method of cosmetically improving the appearance of a part of the body, comprising administering to a subject an amount or dose of microwave energy effective to cosmetically improve the appearance of a part of the body and optionally repeating said treatment until a cosmetically beneficial improvement in appearance has occurred. The method of improving bodily appearance may be used to improve the appearance of a body part comprising a nail or similar structure. In one embodiment, the method of cosmetically improving the appearance of a part of the body may involve improving the appearance of a subject's nails and may be used to remove or correct defects of the nail including misshapen nails, nail ridges, nail narrowing and the like.

Microwave energy according to this invention may have a frequency of between about 500 MHz and about 200 GHz. In other embodiments, the frequency of the microwave energy may range from between about 900 MHz and about 100 GHz. In particular, the frequency of the microwave energy may range from about 2 GHz to about 15 GHz and in a specific embodiment has a frequency of 8 GHz.

It should be understood that the methods of treatment described herein may require the use of a microwave energy having a single frequency or microwave energy across a range of frequencies.

The invention further provides an apparatus for use in treating dermatological conditions, said apparatus comprising a microwave source for providing microwave energy and means for administering or delivering the microwave energy to a subject to be treated. The apparatus provided by this aspect of the invention may be used in any of the therapeutic methods described herein.

Advantageously, the microwave energy emitted or produced by the apparatus elevates or raises the temperature of the subject to be treated. In one embodiment, the microwave energy causes targeted or localised hyperthermia in a tissue of the subject, including, for example the skin and/or sub-ungal tissues. The temperature elevation may be localised to the surface of the skin and/or to the epidermal, dermal and/or sub-dermal and subungal layers thereof (including all minor layers that lie within).

The apparatus may further comprise means for controlling at least one property of the microwave energy produced by the microwave source. For example the means may control or modulate the power, frequency, wavelength and/or amplitude of the microwave energy. The means for controlling the microwave energy may be integral with the apparatus or separately formed and connectable thereto.

In one embodiment, the microwave energy source may produce microwave energy at a single frequency and/or microwave energy across a range of frequencies. The means for controlling at least one property of the microwave energy may permit the user to select or set a particular microwave or microwaves to be produced by the apparatus and/or the properties of the microwave(s) produced.

The apparatus may further comprise means for monitoring the microwave energy produced or generated by the microwave source. For example, the apparatus may include a display indicating one or more properties of the microwave energy.

The intended dosage of microwave energy may be in the range 1-100 W. The energy could be applied continuously for a period of time that may be fixed or may be controlled by the user. The energy may be provided in continuous or pulsed doses or combinations thereof and/or as combinations including increasing and/or or decreasing energy treatment profiles.

In one embodiment, the treatment regime may comprise a number of single applications of microwave energy typically lasting between about 1 to 59 seconds (for example 1-10 s, 20 s, 30 s, 40 s or 50 s and few minutes (for example 1-60 minutes, for example 5 min, 10 min, 15 min, 20 min, 30 min or 45 min) depending upon the energy dosage or the treatment cycle (typically less than 30 minutes). A repeat treatment may be required in the event of the condition recurring.

In another embodiment the treatment method described herein may comprise the application of a low level of energy for a prolonged time period, for example from about 10 min to about 30 minutes or longer to create a low level cutaneous burn. This can typically be achieved for temperatures as low as about 40° C. to about 50° C. (for example at about 46° C.).

In an alternative embodiment the treatment method described herein may comprise the application of a short burst of high level energy to create an instantaneous tissue insult with highly localised and controllable necrosis.

In one embodiment, the means for administering or delivering the microwave energy to a subject to be treated comprises an applicator formed, adapted and/or configured to deliver or administer microwave energy to the subject.

The means for delivering microwave energy may electrically match the range of epsilon relative (relative permittivity) values of the tissue affected by a dermatological condition. In this way, it is possible to ensure efficient delivery of the microwave energy to the tissue.

Advantageously, the means for delivering the microwave energy to a subject may comprise a component or part for contact with a subject to be treated. The part or component for contact with the subjected to be treated may be removable such that it can be discarded or sterilised after use. In one embodiment, the means for delivering the microwave energy may comprise a single application element or a hand piece which accepts a removable tip which can either be a single use, disposable component or a reusable component intended to be sterilized between uses. Advantageously, the part or component for contact with the subject to be treated may comprise a reuse mitigation function to prevent accidental or attempted reuse.

In one embodiment, the part or component for contact with the subject to be treated may be shaped, formed or adapted so as to be compatible with a particular body part, surface or contour thereof. For example, the part or component may comprise a thin, curved or round surface, compatible with the physical properties or profile of an internal or external body part or a surface thereof, including, for example the sinus unguis.

Alternatively the part or component for contact with the subjected to be treated may be shaped, formed or adapted so as to be compatible with a 3 mm Lempert elevator which is typically used to apply phenol.

The means for delivering the microwave energy to a subject may be connected to the microwave source via a flexible cable. In one embodiment the means for delivering the microwave energy to a subject (i.e. the applicator) may be connected to the microwave source via a flexible cable with locking connections having both microwave and signal data cables and may be reversible to enable connection to either port.

In one embodiment the invention provides an apparatus for delivering microwave energy to keratinised tissues or structures—particularly tissues or structures exhibiting symptoms of any of the diseases described herein; the apparatus comprising: —a microwave source for providing microwave energy, connectable to a system controller for controlling at least one property of the microwave radiation provided by the microwave source; and a monitoring system for monitoring the delivery of energy and an applicator means, for example an applicator device, for delivering microwave energy, wherein: —the applicator is configured to deliver precise amounts of microwave energy provided by the source at a single frequency or across a range of frequencies.

Any feature in one aspect of the invention may be applied to any other aspect of the invention, in any appropriate combination. For example, apparatus features may be applied to method features and vice versa.

DETAILED DESCRIPTION

The present invention will now be described in detail with reference to the following figures.

Figure 1:
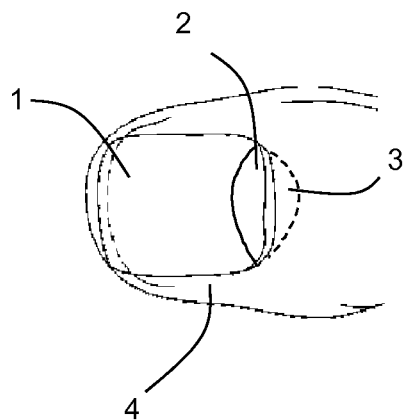
FIG. 1 is a schematic illustration of the anatomy of the nail
Figure 1:
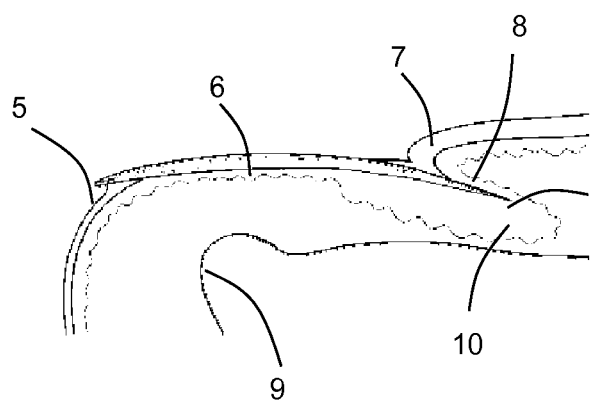

The anatomy of the nail is illustrated in FIG. 1, this comprises the nail plate (corpus unguis) 1, the Lateral horns (Lunula) 2, the nail root (germinal matrix), (radix unguis) 3, the lateral nail fold (Paronychium), 4, the quick (Hyponychium) 5, the nail bed (sterile matrix) 6, the cuticle (Eponychium) 7, the nail cleft (sinus unguis) 8 the periosteum 9, the ventral floor 10.

Figure 2:
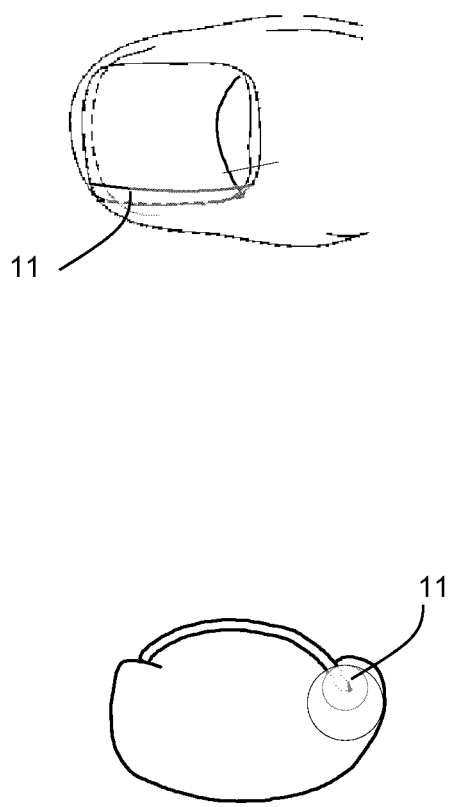
FIG. 2 is a schematic illustration of an ingrown toenail

An illustration of Onychocryptosis is presented in FIG. 2, in this diagrammatic view a section of the nail 11 has grown into the nail wall resulting in swelling and algia.

Figure 3:
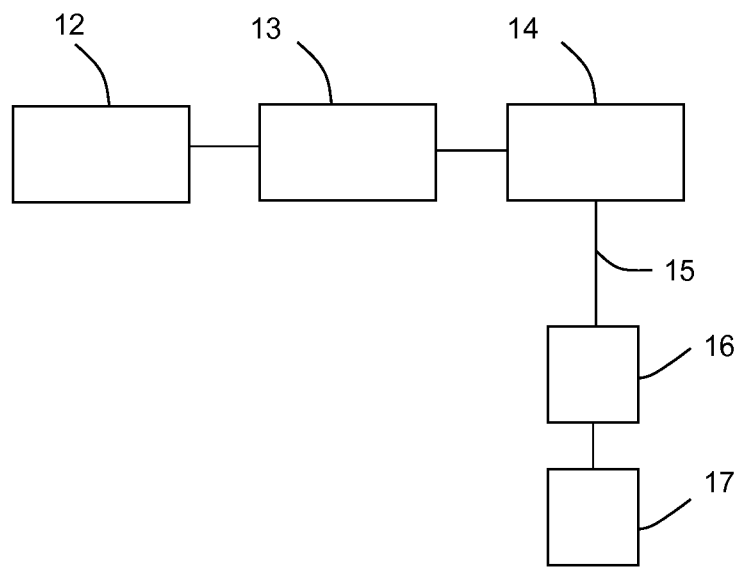
FIG. 3 is a schematic illustration of an embodiment of a microwave treatment system

An embodiment of a microwave power generator system for medical applications is illustrated in FIG. 3. The apparatus comprising: —a microwave source for providing microwave energy 12, connectable to a system controller 13 for controlling at least one property of the microwave radiation provided by the microwave source; and a monitoring system 14 for monitoring the delivery of energy and an interconnecting cable 15 and an applicator hand piece 16 and a removable applicator means 17, for example an applicator device, for delivering microwave energy, wherein: —the applicator is configured to deliver precise amounts of microwave energy provided by the source at a single frequency or across a range of frequencies.

The source in one embodiment comprises a Micronetics MW500-1388 oscillator connected to an Empower BBM5K8CGM amplifier. In alternative embodiments, any suitable oscillator or other source can be used, for example any dielectric resonator oscillator (DRO) or any crystal oscillator (XO) provided they possess the desired frequency bandwidth.

The amplifier in one embodiment is connected to a microwave circulator, for example an MECA CS-6.000 which permit the flow of signals in one direction and a microwave coupler, for example an MECA 722N-30-3.100.

The microwave coupler and microwave circulator are connectable to a transmission line, in the form of high frequency coaxial cable (for example having 50Ω impedance, in this case Huber+Suhner SUCOFLEX 400) having a physical length (and associated electrical phase length), which is arranged to deliver high power energy to the applicator device (for example a ceramic microwave applicator based upon pacific ceramics PD-160 material) or other load, such as an antenna, probe or other radiator of energy. The controller may be a suitably programmed PC or other computer, or a dedicated hardware device, and is operable to control operation of the oscillator and/or the amplifier, thereby to control one or more properties of the microwave radiation generated by the microwave source. The monitoring system may include forward and reverse power measurement circuits that comprise diode detector devices (in this case, an Agilent 33330C Option 003) that are operable to measure forward and reverse signals at a port of the microwave coupler. Any other suitable monitoring system may be provided. The controller is operable to control the source to output microwave radiation at a desired frequency or range of frequencies, at a desired power level and for a desired period of time.

Figure 4:
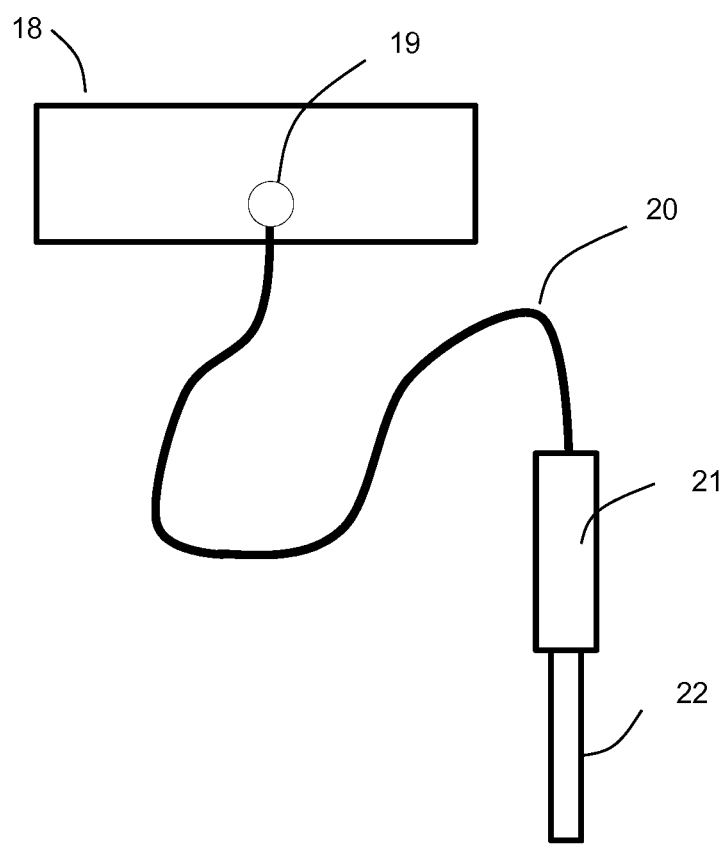
FIG. 4 is a schematic illustration of functional representation of a microwave treatment system for application to treat Onychocryptosis and other dermatological conditions.

FIG. 4 shows the components of an apparatus according to an embodiment of the present invention, the components shown separately for ease of reference. The apparatus comprises a generator system 18 with a locking microwave connection 19 to a flexible microwave cable 20 connected to a hand piece 21 (which may have the same type of locking connection) which accepts an applicator component 22. The applicator component is designed to match to the tissue properties of the germinal matrix 3. The cable 20 may include both microwave and signal data cables and may be reversible to enable connection to either port. The applicator component may dimensionally similar to a lempert elevator.

Figure 5:
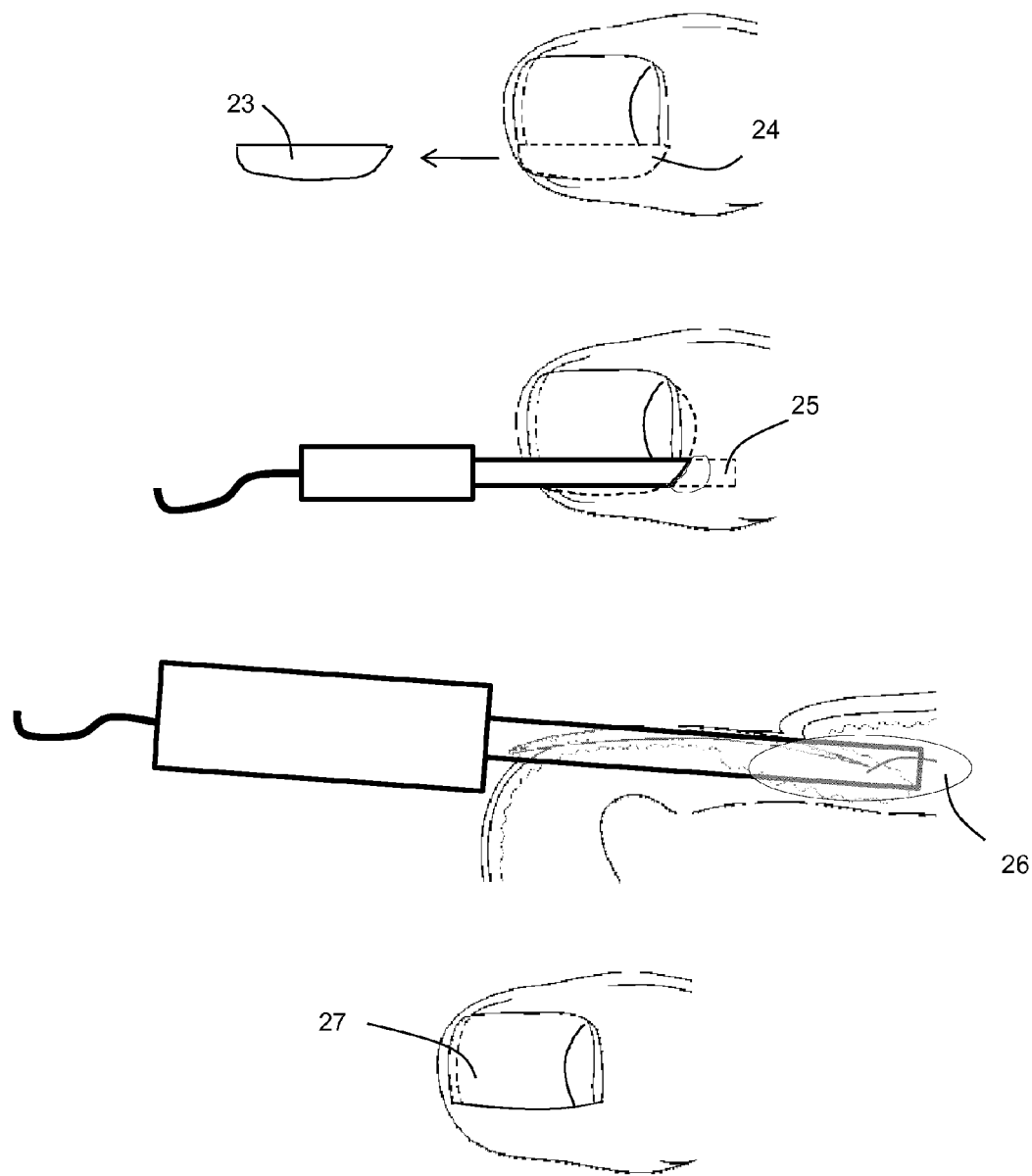
FIG. 5 is a schematic illustration of a microwave partial matrixectomy treatment for Onychocryptosis.

FIG. 5 shows an embodiment of a microwave treatment for Onychocryptosis. In this embodiment a segment of the ingrown nail is conventionally excised to allow access to the radix unguis 24. A microwave applicator 22 is introduced under the eponychium 25 and microwave energy is applied to the germinal matrix 26 producing targeted tissue damage and permanently preventing regrowth of the nail keratin. The narrower nail 27 releases the lateral pressure on the paronychium tissue resolving the onychocryptosis condition. The treatment can be single sided or double sided depending upon the extent of the onychocryptosis. The microwave frequency chosen will be sufficient that the penetration of energy will be limited to the germinal matrix to prevent damage to the underlying tissues such as the periosteum or other tissues that are not intended to be ablated.

Figure 6:
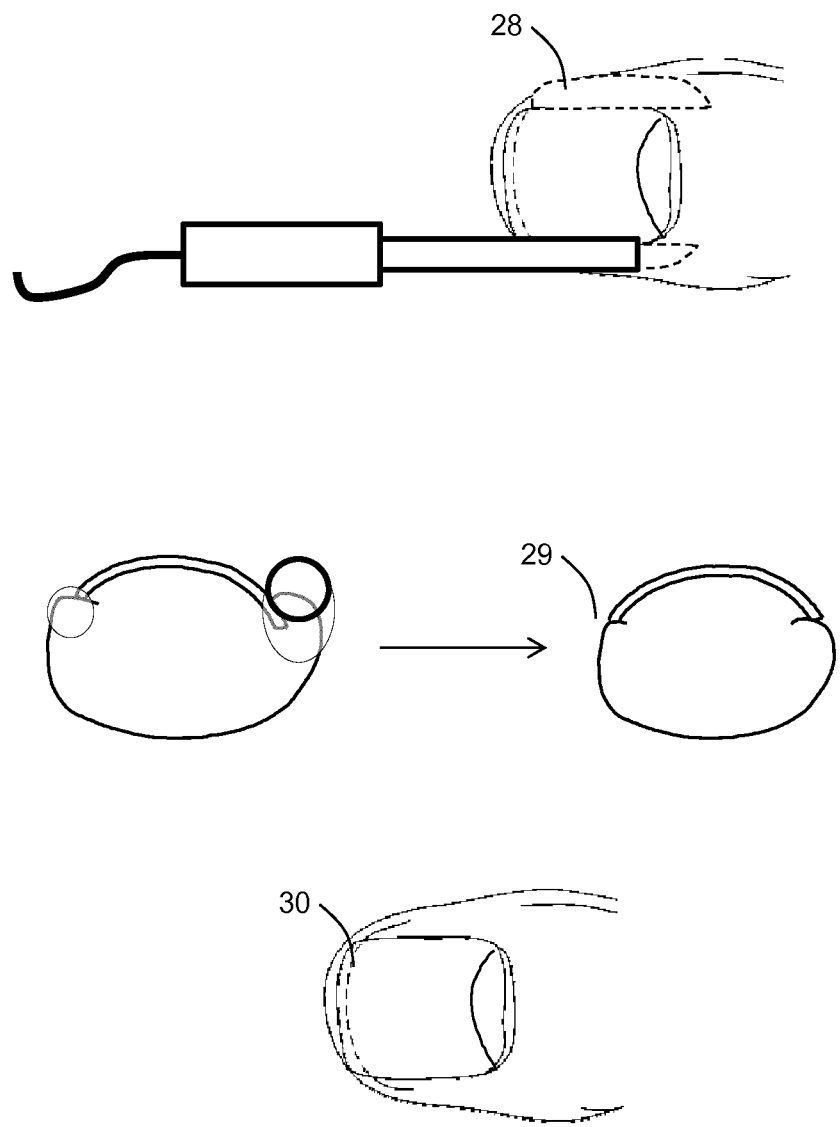
FIG. 6 is a schematic illustration of the microwave assisted Vandenbos procedure.

An alternative embodiment of a microwave onychocryptosis treatment is illustrated in FIG. 6 where a microwave applicator 22 is used to ablate the paronychium tissue 28 at the side of the nail, leaving the nail intact and removing the lateral pressure against the nail 29, resulting in a more cosmetically attractive result as the nail is intact and is symmetrical. This technique is hereby referred to as a microwave assisted vandenbos procedure.

It will be understood that embodiments of the present invention have been described above purely by way of example, and modifications of detail can be made within the scope of the invention.

Each feature disclosed in the description, and (where appropriate) the claims and drawings may be provided independently or in any appropriate combination.

The invention claimed is:

1. A method of treating or preventing onychocryptosis, said method comprising administering to a subject having/suffering from onychocryptosis, a dose of microwave energy between 1 W and 100 W, wherein the microwave energy has a frequency of between about 500 MHz and about 200 GHz;
   wherein the administering of the dose of microwave energy comprises applying microwave energy to the subject's germinal matrix to damage the germinal matrix to prevent regrowth of all or part of a nail, and wherein the microwave energy prevents damage to underlying tissues.

2. The method of claim 1, wherein the onychocryptosis occurs as a complication of a microbial infection, a genetic condition/abnormality, an allergic condition/disorder, an autoimmune disease and/or cancer.

3. The method of claim 1, wherein the treatment comprises repeated rounds of treatment with microwave energy.

4. The method of claim 1, wherein the microwave energy comprises a single frequency or a range of different frequencies.

5. The method of claim 1, wherein the microwave energy has a frequency of about 8 GHz.

6. The method of claim 1, wherein the microwave energy is applied as a continuous or pulsed dose.

7. The method of claim 1, wherein each dose of microwave energy comprises microwave energy having an increasing or decreasing energy profile.

* * * * *